(12) United States Patent
Prema Mohanasundaram

(10) Patent No.: US 12,004,746 B2
(45) Date of Patent: Jun. 11, 2024

(54) ANVIL BUTTRESS ATTACHMENT FOR SURGICAL STAPLING APPARATUS

(71) Applicant: Covidien LP, Mansfield, MA (US)

(72) Inventor: Suresh Kumar Prema Mohanasundaram, Chennai (IN)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/989,066

(22) Filed: Nov. 17, 2022

(65) Prior Publication Data

US 2023/0080138 A1  Mar. 16, 2023

Related U.S. Application Data

(63) Continuation of application No. 17/140,481, filed on Jan. 4, 2021, now Pat. No. 11,534,170.

(51) Int. Cl.
*A61B 17/072* (2006.01)
(52) U.S. Cl.
CPC ........... *A61B 17/07292* (2013.01); *A61B 2017/07257* (2013.01); *A61B 2017/07271* (2013.01)
(58) Field of Classification Search
CPC .... A61B 17/07292; A61B 2017/07257; A61B 2017/07271
See application file for complete search history.

(56) References Cited

U.S. PATENT DOCUMENTS

| 3,054,406 | A | 9/1962 | Usher |
|---|---|---|---|
| 3,124,136 | A | 3/1964 | Usher |
| 3,364,200 | A | 1/1968 | Ashton et al. |
| 3,499,591 | A | 3/1970 | Green |
| 3,797,494 | A | 3/1974 | Zaffaroni |
| 3,939,068 | A | 2/1976 | Wendt et al. |

(Continued)

FOREIGN PATENT DOCUMENTS

| CA | 2282761 A1 | 9/1998 |
|---|---|---|
| DE | 1602563 U | 3/1950 |

(Continued)

OTHER PUBLICATIONS

European Office Action corresponding to EP 14 17 2681.0 dated May 13, 2016.

(Continued)

*Primary Examiner* — Michelle Lopez
(74) *Attorney, Agent, or Firm* — Carter, DeLuca & Farrell, LLP

(57) ABSTRACT

An anvil buttress loading system includes an anvil assembly, an anvil buttress loading tool, and an anvil buttress. The anvil buttress is releasably retained on the anvil buttress loading tool with a body of the anvil buttress is positioned on a base of the anvil buttress loading tool, a proximal tab of the anvil buttress positioned over a loading ramp of the anvil buttress loading tool, and a distal tab of the anvil buttress positioned within a flange of the anvil buttress loading tool. The anvil buttress is transferrable from the anvil buttress loading tool to the anvil assembly such that the anvil buttress is releasably secured to the anvil assembly with the body positioned on a tissue facing surface of the anvil assembly, the proximal tab engaged with a pin assembly of the anvil assembly, and the distal tab engaged with an anvil tip of the anvil assembly.

17 Claims, 8 Drawing Sheets

(56) References Cited

U.S. PATENT DOCUMENTS

| | | |
|---|---|---|
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A * | 8/1996 | McKean .......... A61B 17/07207 227/19 |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,240 A | 9/1998 | Robertson |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,865,361 A | 2/1999 | Milliman et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A * | 8/2000 | Gabbay ............ A61B 17/07207 227/176.1 |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,231,565 B1 | 5/2001 | Tovey et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 * | 8/2001 | Dalessandro .......... A61L 31/06 606/139 |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 * | 3/2004 | Myers ............. A61B 17/07207 361/776 |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |

(56) References Cited

U.S. PATENT DOCUMENTS

| | | |
|---|---|---|
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |

(56) References Cited

U.S. PATENT DOCUMENTS

| | | |
|---|---|---|
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,828,023 B2 | 9/2014 | Neff et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0025816 A1* | 2/2006 | Shelton, IV ...... A61B 17/07207 606/215 |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1* | 10/2007 | Pace-Floridia ........ A61L 31/048 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |

(56) References Cited

U.S. PATENT DOCUMENTS

| | | |
|---|---|---|
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2008/0308608 A1 | 12/2008 | Prommersberger |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0221062 A1 | 8/2013 | Hodgkinson |
| 2013/0256379 A1 | 10/2013 | Schmid et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1* | 8/2015 | Racenet ............ A61B 17/07292 227/175.1 |
| 2015/0327864 A1 | 11/2015 | Hodgkinson et al. |
| 2015/0327865 A1* | 11/2015 | Marczyk ............ A61B 17/105 227/176.1 |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0250001 A1 | 9/2018 | Aronhalt et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| EP | 3552558 A1 | 10/2019 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |
| WO | 2022086842 A2 | 4/2022 |

OTHER PUBLICATIONS

Extended European Search Report corresponding to EP 16 15 3647.9 dated Jun. 3, 2016.

Chinese Office Action corresponding to CN 201210545228 dated Jun. 29, 2016.

Japanese Office Action corresponding to JP 2012-250058 mailed Jun. 29, 2016.

European Office Action corresponding to EP 14 15 7997.9 dated Jun. 29, 2016.

Canadian Office Action corresponding to CA 2,712,617 dated Jun. 30, 2016.

Chinese First Office Action corresponding to CN 2013103036903 dated Jun. 30, 2016.

Australian Patent Examination Report No. 1 corresponding to AU 2012250278 dated Jul. 10, 2016.

Australian Patent Examination Report No. 1 corresponding to AU 2012244382 dated Jul. 10, 2016.

Japanese Office Action corresponding to 2012-255242 dated Jul. 26, 2016.

Japanese Office Action corresponding to JP 2012-268668 dated Jul. 27, 2016.

European Office Action corresponding to EP 14 15 2060.1 dated Aug. 4, 2016.

European Office Action corresponding to EP 12 16 5609.4 dated Aug. 5, 2016.

European Office Action corresponding to EP 15 15 2392.5 dated Aug. 8, 2016.

Japanese Office Action corresponding to JP 2013-003624 dated Aug. 25, 2016.

Australian Patent Examination Report No. 1 corresponding to AU 2012261752 dated Sep. 6, 2016.

Japanese Office Action corresponding to JP 2014-252703 dated Sep. 26, 2016.

(56) References Cited

OTHER PUBLICATIONS

European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.

(56) References Cited

OTHER PUBLICATIONS

Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Partial European Search Report issued in corresponding European Application No. 21217391.8 dated Jun. 7, 2022, 14 pages.
Extended European Search Report issued in corresponding European Application No. 21217391.8 dated Sep. 7, 2022, 13 pages.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.

(56) References Cited

OTHER PUBLICATIONS

Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

* cited by examiner

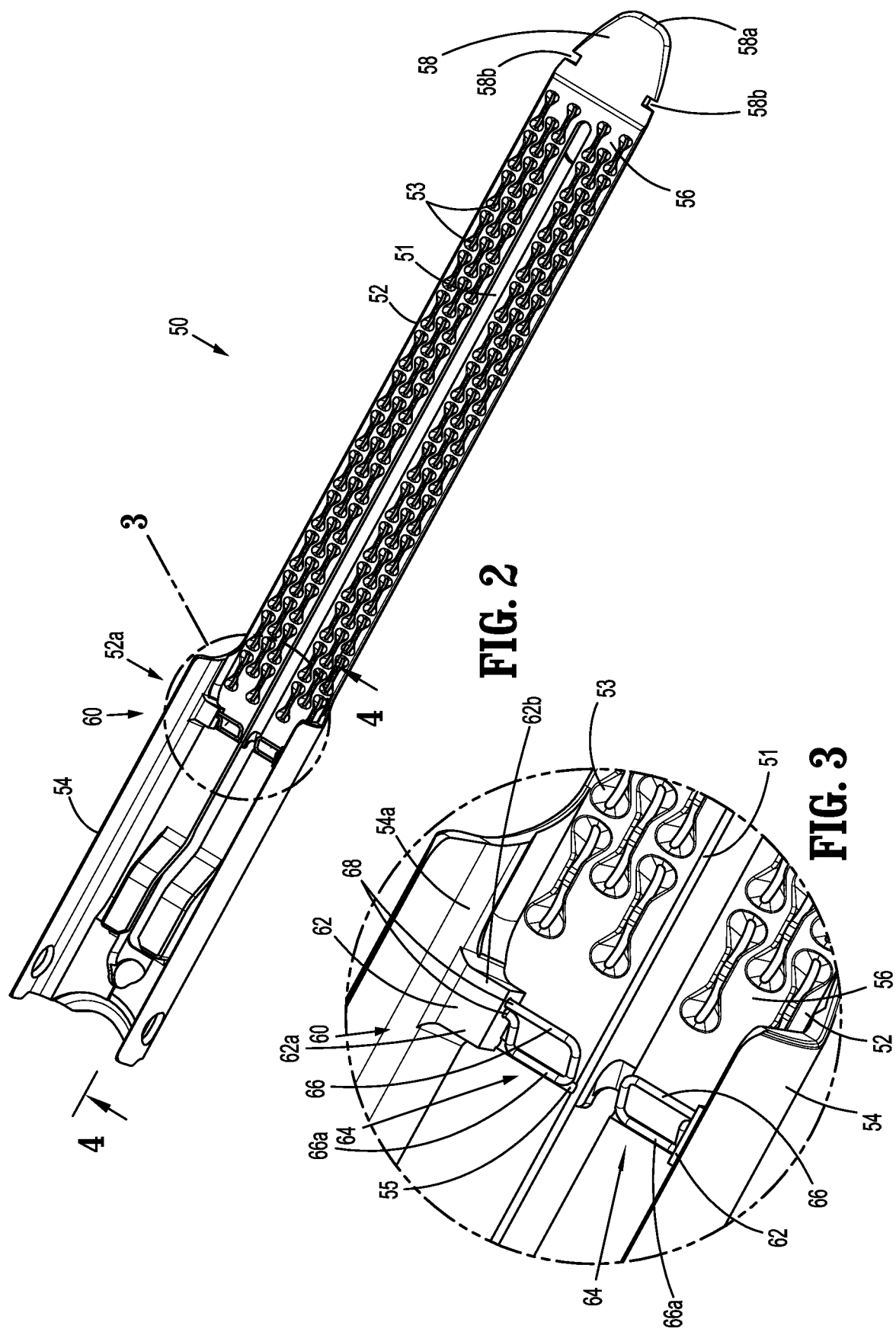

ANVIL BUTTRESS ATTACHMENT FOR SURGICAL STAPLING APPARATUS

CROSS-REFERENCE TO RELATED APPLICATIONS

The present disclosure is a continuation of U.S. patent application Ser. No. 17/140,481, filed on Jan. 4, 2021, the entire contents of which is incorporated by reference herein.

FIELD

The present disclosure relates generally to surgical devices, and more particularly, to anvil buttress attachment systems, assemblies, and methods for releasably securing an anvil buttress to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach buttress material(s) to the surgical stapling apparatus in the operating room during a surgical procedure, or utilize a surgical stapling apparatus including the buttress material(s) pre-installed thereon, e.g., by an expensive automated attachment process. The buttress material reinforces the staple or suture line as well as covers the juncture of the tissues to reduce leakage prior to healing.

SUMMARY

The present disclosure relates to anvil side buttress material attachment onto a jaw assembly of a surgical stapling apparatus. Anvil buttress attachment systems, assemblies, and methods of the present disclosure are designed to provide robust, releasable mechanical attachment of an anvil buttress to an anvil assembly, and to make anvil side buttress material attachment in the operating room a simple, straight-forward, and cost-effective procedure.

In one aspect, the present disclosure provides an anvil buttress loading system including an anvil assembly, an anvil buttress loading tool, and an anvil buttress. The anvil assembly includes an anvil plate and an anvil tip. The anvil plate has a tissue facing surface with a proximal end portion of the tissue facing surface including a pin assembly. The anvil buttress loading tool includes a base having a support surface, a loading ramp extending proximally of the base, and a flange extending distally from the base. The anvil buttress includes a body, a proximal tab extending proximally from the body, and a distal tab extending distally from the body. The anvil buttress is releasably retained (e.g., pre-loaded) on the anvil buttress loading tool with the body positioned on the support surface, the proximal tab positioned over the loading ramp, and the distal tab positioned within the flange. The anvil buttress is transferrable from the anvil buttress loading tool to the anvil assembly such that the anvil buttress is releasably secured to the anvil assembly with the body positioned on the tissue facing surface, the proximal tab engaged with the pin assembly, and the distal tab engaged with the anvil tip.

The pin assembly of the anvil assembly may include a pair of retaining pins disposed on opposed sides of a central longitudinal slot defined through the tissue facing surface of the anvil plate. Each retaining pin may include a body positioned against the tissue facing surface and movable relative thereto. The bodies of the pair of retaining pins are configured to hold the proximal tab of the anvil buttress against the tissue facing surface. The tissue facing surface of the anvil assembly may include a groove defined therein. The bodies of the pair of retaining pins may be biased to extend into the groove. Each retaining pin may include an arm extending laterally from the body and secured to the anvil assembly. Each of the bodies of the pair of retaining pins may be disposed at an angle relative to the tissue facing surface of the anvil assembly.

The loading ramp of the anvil buttress loading tool may include a proximal end and a sloped surface sloping upwardly and distally from the proximal end to a distal end of the loading ramp. The loading ramp may be configured to move the bodies of the pair of retaining pins off of the tissue facing surface of the anvil assembly during transfer of the anvil buttress to the anvil assembly. The loading ramp may be coupled to the base by a post, and a pair of apertures may be defined on opposed sides of the post between the base and the loading ramp. The bodies of the pair of retaining pins may be configured to follow the sloped surface of the loading ramp and pass into the pair of apertures during transfer of the anvil buttress to the anvil assembly.

The flange of the anvil buttress loading tool may be disposed at an angle relative to the base. A distal opening may be defined through the flange of the anvil buttress loading tool and a distal window may be defined through the distal tab of the anvil buttress. The distal window may be aligned with the distal opening such that during transfer of the anvil buttress to the anvil assembly, the anvil tip of the anvil assembly engages the distal tab through the distal window.

In another aspect, the present disclosure provides an anvil buttress loading assembly including an anvil buttress loading tool and an anvil buttress. The anvil buttress loading tool includes a base having a support surface, a loading ramp extending proximally of the base, and a flange extending distally from the base. The anvil buttress includes a body, a proximal tab extending proximally from the body, and a distal tab extending distally from the body. The body of the anvil buttress is positioned on the support surface, the proximal tab of the anvil buttress is positioned over the loading ramp, and the distal tab is positioned within the flange.

The loading ramp may include a proximal end and a sloped surface sloping upwardly and distally from the proximal end to a distal end of the loading ramp. The loading ramp may be coupled to the base by a post, and a pair of apertures may be defined on opposed sides of the post between the base and the loading ramp.

The flange may extend at an angle relative to the base. A distal opening may be defined through the flange of the anvil buttress loading tool and a distal window may be defined through the distal tab of the anvil buttress. The distal window may be aligned with the distal opening.

In yet another aspect, a tool assembly includes a staple cartridge assembly, an anvil assembly, and an anvil buttress. The anvil assembly includes an anvil plate and an anvil tip. The anvil plate has a tissue facing surface with a proximal end portion of the tissue facing surface including a pin assembly. The anvil buttress includes a body disposed over the tissue facing surface, a proximal tab releasably coupled to the anvil assembly by the pin assembly, and a distal tab releasably coupled to the anvil tip.

The pin assembly of the anvil assembly may include a pair of retaining pins disposed on opposed sides of a central longitudinal slot defined through the tissue facing surface of the anvil plate. Each retaining pin may include a body positioned against the tissue facing surface and movable relative thereto, the bodies of the pair of retaining pins holding the proximal tab of the anvil buttress against the tissue facing surface. The tissue facing surface of the anvil assembly may include a groove defined therein. The bodies of the pair of retaining pins may be biased to extend into the groove. Each retaining pin may include an arm extending laterally from the body and secured to the anvil assembly. Each of the bodies of the pair of retaining pins may be disposed at an angle relative to the tissue facing surface of the anvil assembly.

The anvil buttress may include a distal window defined through the distal tab. The distal tab may be coupled to the anvil assembly by engagement of the distal tab around the anvil tip through the distal window.

The details of one or more aspects of the disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

FIG. 2 is a bottom, perspective view of an anvil assembly of the tool assembly of FIG. 1;

FIG. 3 is a close-up view of the area of detail indicated in FIG. 2, illustrating a pin assembly of the anvil assembly;

DETAILED DESCRIPTION

Figure 1:
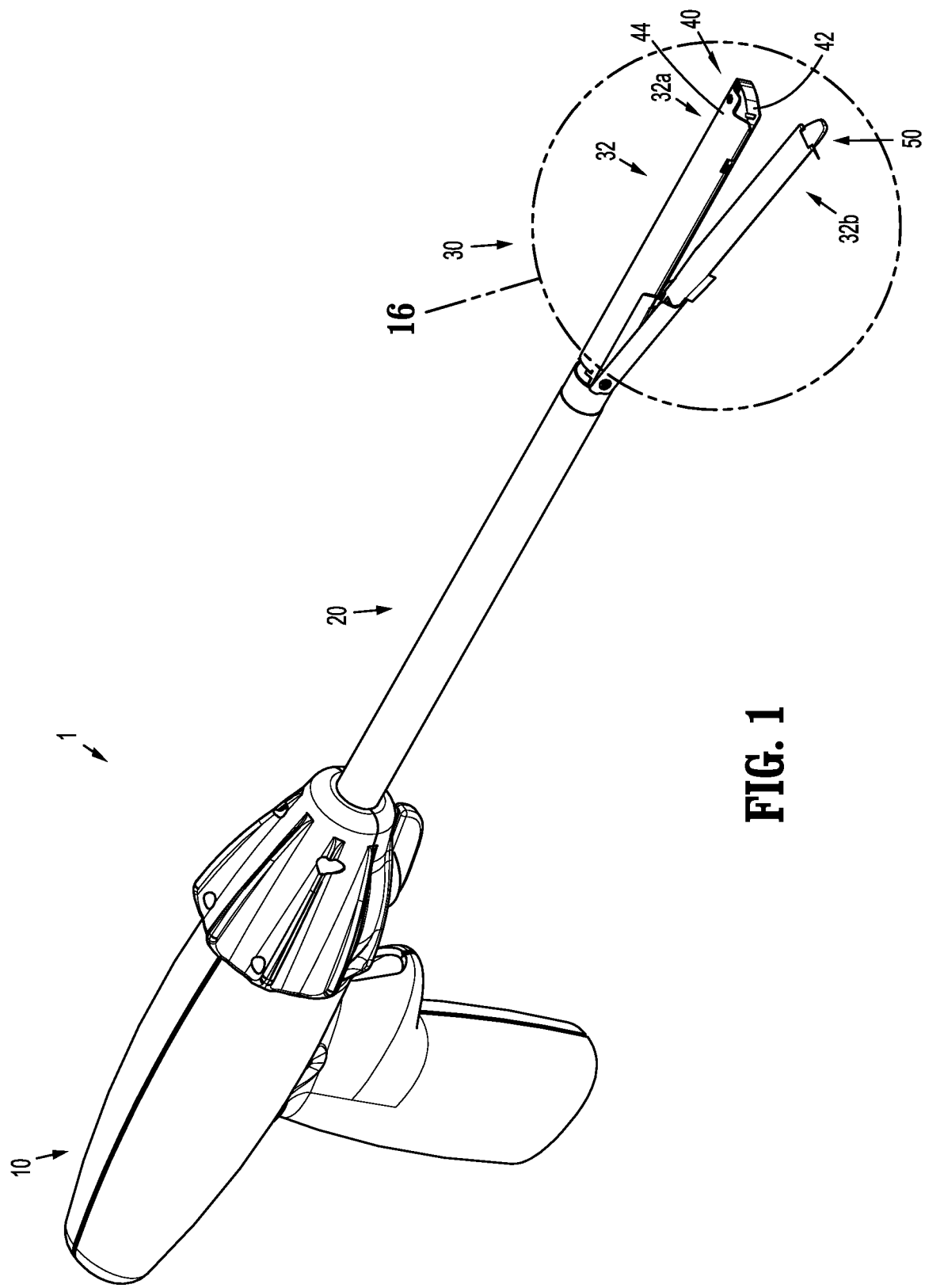
FIG. 1 is a perspective view of a surgical stapling apparatus including a tool assembly in accordance with an aspect of the present disclosure.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user.

Referring now to FIG. 1, an exemplary surgical stapling apparatus or surgical stapler 1 is shown for use in stapling tissue in accordance with aspects of the present disclosure. The surgical stapling apparatus 1 will be described to the extent necessary to disclose aspects of the present disclosure.

The surgical stapling apparatus 1 generally includes a handle assembly 10, an elongate tubular body 20 extending distally from the handle assembly 10, and a loading unit 30 extending distally from the elongate tubular body 20. The handle assembly 10 may be manually driven or may be powered (e.g., by an electric motor). For a detailed description of the structure and function of exemplary surgical stapling apparatus, including exemplar manual and powered handle assemblies, exemplar elongate tubular bodies, and exemplar loading units, reference may be made to U.S. Pat. Nos. 5,762,256, 5,865,361, and 9,918,713, the entire contents of each of which are incorporated herein by reference.

It should be appreciated that principles of the present disclosure are equally applicable to surgical stapling apparatus having other configurations such as, for example, the types described in U.S. Pat. Nos. 5,810,240 and 7,334,717, the entire contents of each of which are incorporated herein by reference. Accordingly, it should be understood that a variety of surgical stapling apparatus may be utilized with aspects of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with aspects of the present disclosure.

The loading unit 30 may also be configured for use with other surgical apparatus, such as robotic devices/instruments. For a detailed description of the structure and function of exemplary robotic systems, reference may be made to U.S. Pat. Nos. 6,231,565 and 8,828,023, the entire contents of each of which are incorporated herein by reference.

The loading unit 30 includes a tool or jaw assembly 32 including first and second jaw members 32a, 32b. One or both of the first and second jaw members 32a, 32b is pivotable with respect to the other such that the tool assembly 32 is movable between an open position in which the first and second jaw members 32a, 32b are spaced apart with respect to each other, and a closed position in which the first and second jaw members 32a, 32b are substantially adjacent each other.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 42) of the MULU is replaced after each staple and cut operation of the surgical stapling apparatus 1 a pre-determined number of times before the entire MULU is replaced. Alternatively, the loading unit 30 may be permanently affixed to the elongated tubular body 20.

The first jaw member 32a of the tool assembly 32 includes a staple cartridge assembly 40 and the second jaw member 32b of the tool assembly 32 includes an anvil assembly 50. The staple cartridge assembly 40 includes a staple cartridge 42 that may be removably and/or replaceably attached to a cartridge carrier 44 of the staple cartridge assembly 40. The staple cartridge 42 may be any staple cartridge used in surgical stapling apparatus within the purview of those skilled in the art that includes a plurality of fasteners (e.g., staples) releasably disposed therein.

Figure 4:
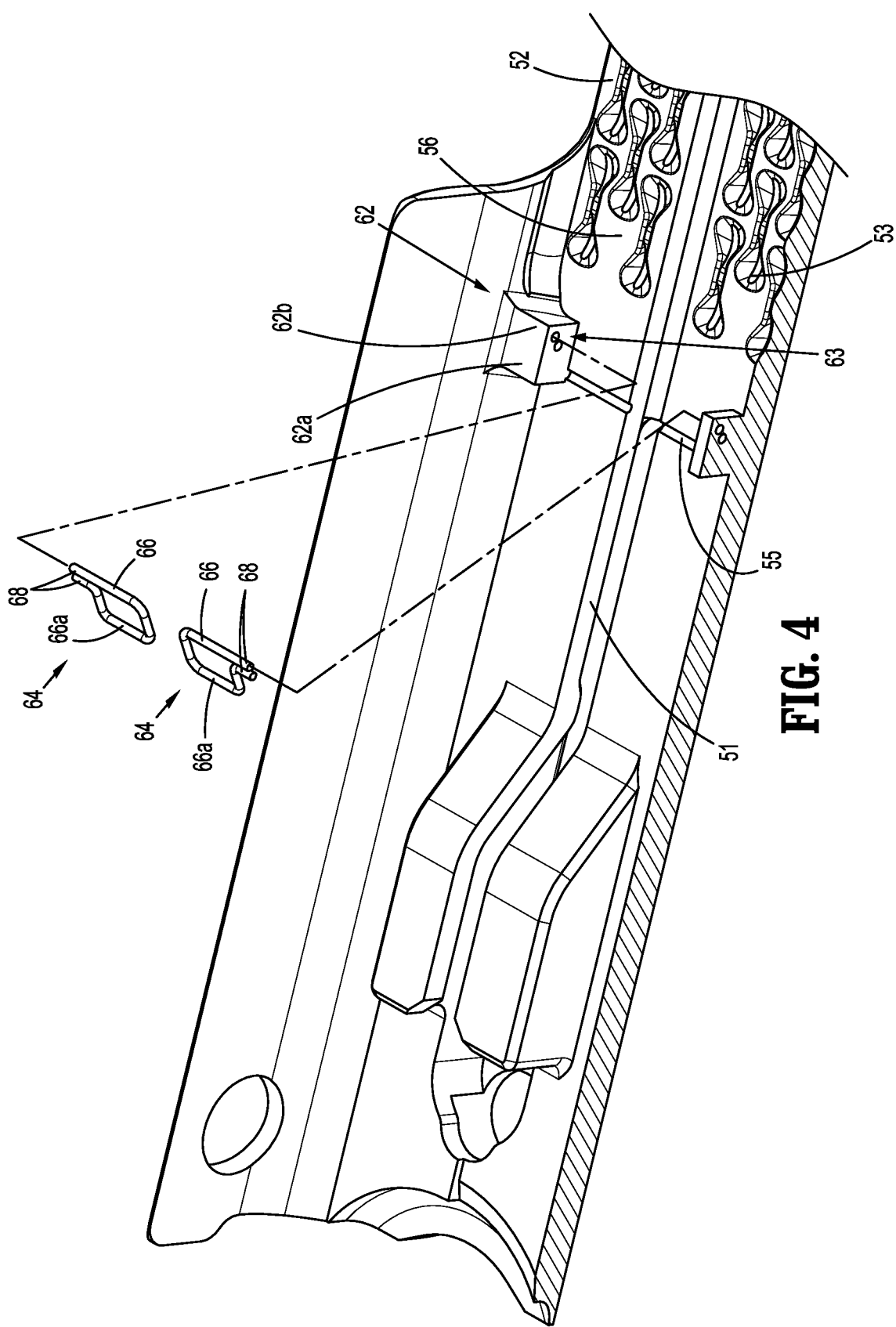
FIG. 4 is a perspective view of the anvil assembly of FIG. 2, taken along section line 4-4 of FIG. 2, shown with retaining pins of the pin assembly separated from the anvil assembly.

As shown in FIGS. 2-4, the anvil assembly 50 includes an anvil plate 52 and an anvil cover 54 (FIG. 9) secured over the anvil plate 52. The anvil plate 52 has a central longitudinal slot 51 formed therein and a plurality of staple forming pockets or cavities 53 defined in an inward or tissue facing surface 56 thereof. An anvil tip 58 extends distally of the staple forming pockets 53. The anvil tip 58 has a curved leading end 58a and a pair of notches 58b defined in opposed side edges of the anvil tip 58. The pair of notches 58b are configured to releasably secure a distal portion of an anvil buttress to the anvil assembly 50. A proximal portion 52a of the anvil plate 52, which extends proximally of the staple forming pockets 53, includes a groove 55 defined in and extending across the tissue facing surface 56 and a pin assembly 60 configured to releasably secure a proximal portion of an anvil buttress to the anvil assembly 50.

The pin assembly 60 includes a pair of retaining blocks 62 and a pair of retaining pins 64 disposed on opposed sides of the central longitudinal slot 51 of the anvil plate 52. Each retaining block 62 is secured to or integrally formed with an inner side surface 54a of the anvil cover 54. A proximal portion 62a of the retaining block 62 is aligned with the groove 55 of the anvil plate 52 and a distal portion 62b of the retaining block 62 includes one or more pin holes 63 defined in a surface of the retaining block 62 facing the central longitudinal slot 51.

Each retaining pin 64 is formed from a rod of material (e.g., a metal wire) that is pre-formed (e.g., bent) into an open frame including a body 66 having a substantially rectangular shape and a pair of arms 68 extending laterally from the body 66. The retaining pins 64 are formed from a rigid material that is capable of holding its shape and undergoing elastic deformation upon application of a force thereto, as described in detail below. The pair of arms 68 are non-rotatably disposed (e.g., secured) within the pin holes 63 of the retaining blocks 62 and the body 66 extends across the tissue facing surface 56 of the anvil plate 52 between the retaining block 62 and the central longitudinal slot 51, with a segment 66a of the body 66 positioned within the groove 55 defined in the tissue facing surface 56 of the anvil plate 52.

As the groove 55 is disposed proximal to the pin holes 63, the body 66 of the retaining pin 64 is disposed at an angle with respect to the tissue facing surface 56 of the anvil assembly 50. The retaining pin 64 is positioned such that the body 66 is biased to extend into the groove 55. In some aspects, the body 66 is held under strain within the groove 55. The body 66 of the retaining pin 64 is movable out of the groove 55 (e.g., capable of being raised out of the groove 55 and off of the tissue facing surface 56) upon application of a force thereto. The body 66 may be disposed at an acute angle with respect to the portion of the tissue facing surface 56 including the staple forming pockets 53 such that the body 66 is movable upon application of a force in only a proximal direction.

It should be understood that the pin assembly 60 may have other configurations. For example, each retaining pin may include a single arm, the arm(s) of each retaining pin may be directly coupled to the anvil assembly (e.g., the retaining blocks may be omitted), and/or the body of each retaining pin may be sized and shaped to directly abut the tissue facing surface of the anvil assembly (e.g., the groove may be omitted).

Figure 5:
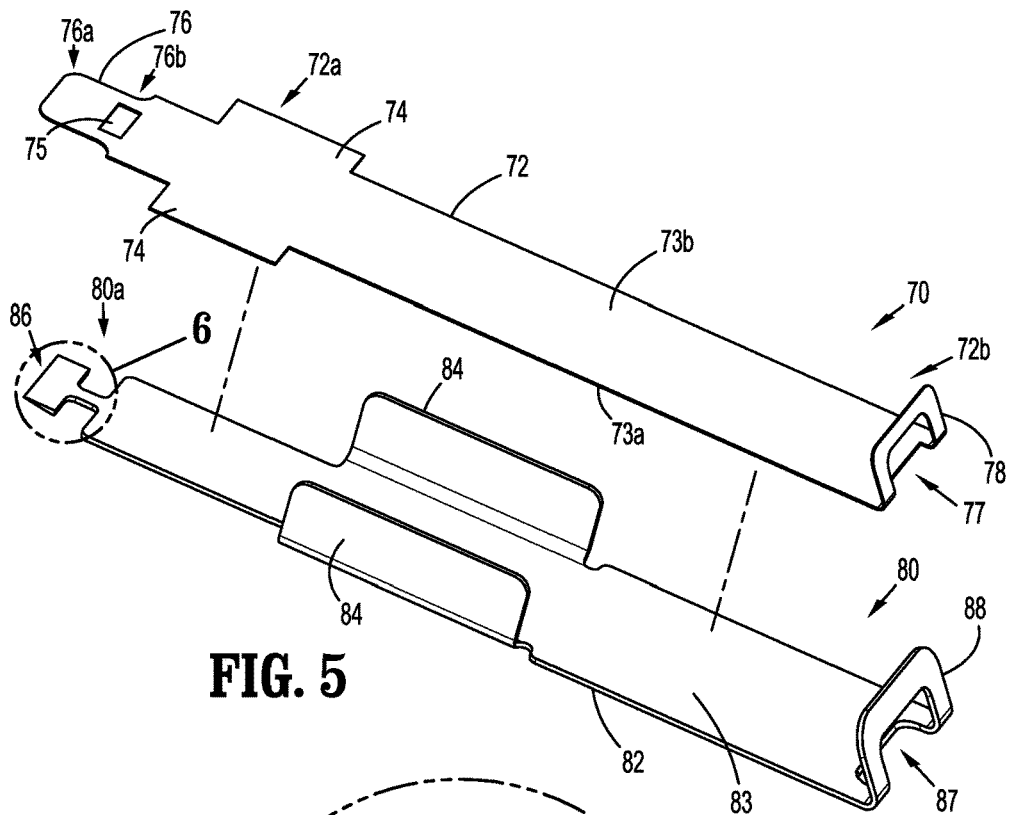
FIG. 5 is a perspective view, with parts separated, of an anvil buttress loading tool and an anvil buttress in accordance with aspects of the present disclosure.

Turning now to FIG. 5, an anvil buttress 70 (also referred to herein generally as a surgical buttress) is shown separated from an anvil buttress loading tool 80 (also referred to herein generally as a loading tool). The anvil buttress 70 includes a body 72 having a tissue contacting surface 73a and an anvil contacting surface 73b. The body 72 has a generally rectangular shape that is sized to cover the tissue facing surface 56 (FIG. 2) of the anvil assembly 50. A pair of wings 74 extend from opposed sides of a proximal portion 72a of the body 72.

A proximal tab 76 extends proximally from the proximal portion 72a of the body 72 and has a smaller width than the body 72. A proximal window 75 is defined in a distal portion 76b of the proximal tab 76. A distal tab 78 extends distally from a distal portion 72b of the body 72. The distal tab 78 is bent to extend at an angle relative to the body 72 and has a distal window 77 defined therethrough. The distal window 77 is sized and shaped to receive the anvil tip 58 (FIG. 2) therethrough. The distal window 77 may be configured so that the distal tab 78 engages the notches 58b (FIG. 2) in the anvil tip 58 to aid in retaining the distal tab 78 thereto. In aspects in which notches 58b are not defined in the anvil tip 58, the distal window 77 is configured so that the distal tab 78 frictionally engages the anvil tip 58. In some aspects, the distal tab 78 may be stiffened to retain the bend relative to the body 72 and, in other aspects, the distal tab 78 is bent relative to the body 72 by positioning the distal tab 78 within a flange 88 of the anvil buttress loading tool 80. In aspects, the distal tab 78 extends at an acute angle relative to anvil facing surface 73b of the body 72 to aid in retaining the distal tab 78 to the anvil tip 58.

The anvil buttress 70 is fabricated from biocompatible materials which are bioabsorbable or non-absorbable, natural or synthetic materials. It should be understood that a single or combination of natural, synthetic, bioabsorbable, and/or non-bioabsorbable materials may be used to form the anvil buttress 70. In aspects, the anvil buttress 70 is formed from a single sheet of material that is cut to shape. In other aspects, the anvil buttress 70 is formed from a plurality of sheets of material, that are fabricated from the same or different materials, and/or the components (e.g., the body, the wings, the tabs, etc.) of the anvil buttress 70 are formed from the same or different materials that are attached to one another by, for example, welding, using adhesive, tying sutures, etc.

The anvil buttress 70 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The anvil buttress 70 may be a single porous or non-porous layer, or include a plurality of layers including any combination of porous and non-porous layers. For example, the anvil buttress may include multiple porous and non-porous layers that are stacked in an alternating manner. In another example, the anvil buttress may be formed in a "sandwich-like" manner wherein the outer layers are porous and the inner layer(s) are non-porous, or vice versa.

Porous layer(s) in a surgical buttress may enhance the ability of the surgical buttress to absorb fluid, reduce bleeding, and/or seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

With continued reference to FIG. 5, the anvil buttress loading tool 80 is configured to releasably retain the anvil buttress 70 thereon and to receive the anvil assembly 50 (FIG. 2) therein for loading the anvil buttress 70 onto the anvil assembly 50 (e.g., transferring the anvil buttress 70 from the anvil buttress loading tool 80 to the anvil assembly 50). The anvil buttress loading tool 80 includes a base 82 having a support surface 83 and longitudinal rails 84 extending from opposed sides of the base 82. The support surface 83 is dimensioned to accommodate the body 72 of the anvil buttress 70 thereon. The longitudinal rails 84 help maintain alignment of the anvil buttress 70 on the anvil buttress loading tool 80 and act as guides during loading and unloading of the anvil buttress loading tool 80 onto and off of the anvil assembly 50.

The anvil buttress loading tool 80 includes a loading ramp 86 at a proximal end 80a thereof and a flange 88 at a distal end 80b thereof. The flange 88 is bent to extend at an angle relative to the base 82 and defines a distal opening 87 therethrough. In aspects, the flange 88 is bent at an acute angle relative to the support surface 83 of the base 82. The flange 88 is configured to receive the distal tab 78 of the anvil buttress 70 therein. The distal opening 87 in the flange 88 is dimensioned to correspond with the dimensions of the distal window 77 in the anvil buttress 70 which, in turn, is dimensioned to receive and frictionally engage the anvil tip 58, as described above.

Figure 6:
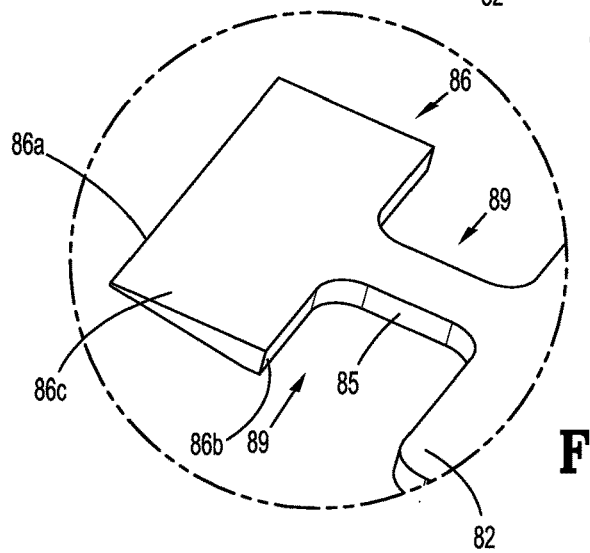
FIG. 6 is a close-up view of the area of detail indicated in FIG. 5, illustrating a loading ramp of the anvil buttress loading tool.

As shown in FIGS. 5 and 6, the loading ramp 86 is interconnected with the base 82 by a post 85 such that a pair of apertures or cut-outs 89 are defined on opposed sides of the post 85 between the base 82 and the loading ramp 86. In aspects, the width of the post 85 corresponds with a width of the central longitudinal slot 51 (FIG. 2) of the anvil assembly 50. The loading ramp 86 includes a proximal end 86a which acts as a camming surface to move the retaining pins 64 (FIG. 3) of the pin assembly 60 of the anvil assembly 50, as described below, and a sloped surface 86c sloping upwardly and distally from the proximal end 86a to a distal end 86b of the loading ramp 86 for guiding the movement of the retaining pins 64 during loading of the anvil buttress 70 onto the anvil assembly 50. The loading ramp 86 and the post 85 are dimensioned to accommodate the proximal tab 76 of the anvil buttress 70 thereon. In some aspects, a proximal portion 76a of the proximal tab 76 is positioned on the loading ramp 86 and the post 85, and the distal portion 76b of the proximal tab 76 is positioned on the base 82.

Figure 7:
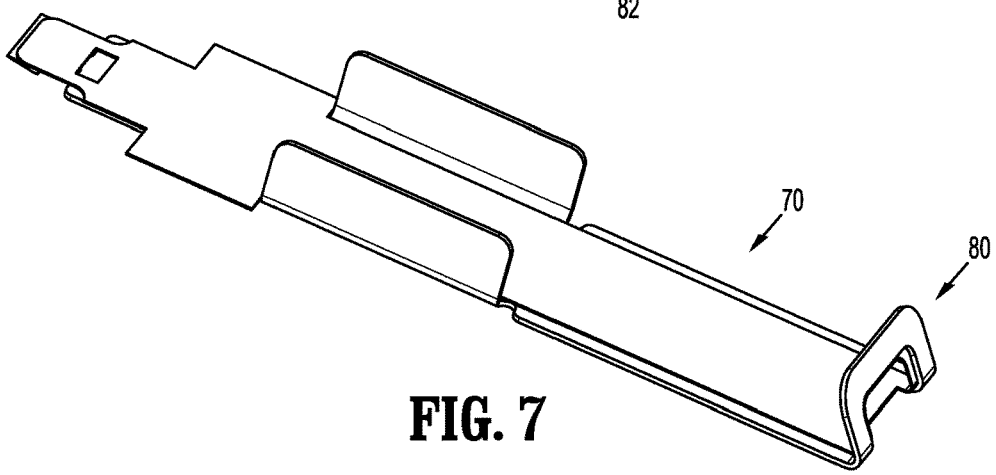
FIG. 7 is a perspective view of the anvil buttress loading tool of FIG. 5, shown loaded with the anvil buttress of FIG. 5.

In a method of loading the anvil buttress loading tool 80 with the anvil buttress 70, the body 72 of the anvil buttress 70 is placed against the support surface 83 of the base 82 with the tissue contacting surface 73a of the anvil buttress 70 in contact with the support surface 83 and the pair of wings 74 disposed proximal to the longitudinal rails 84. With the body 72 of the anvil buttress 70 positioned on the support surface 83, the proximal tab 76 of the anvil buttress 70 is positioned on the loading ramp 86 and the distal tab 78 is positioned within the flange 88 such that the distal window 77 is aligned or in registration with the distal opening 87 of the flange 88. The loaded configuration of the anvil buttress 70 on the anvil buttress loading tool 80 is shown in FIG. 7. The anvil buttress 70 is releasably retained on the anvil buttress loading tool 80 by, for example, static friction, modification of the surface characteristics (e.g., texture) of the anvil buttress loading tool for gripping of the anvil buttress, application of a light adhesive or adhesive with low aggressiveness between the anvil buttress loading tool and the anvil buttress, etc.

Figure 8:
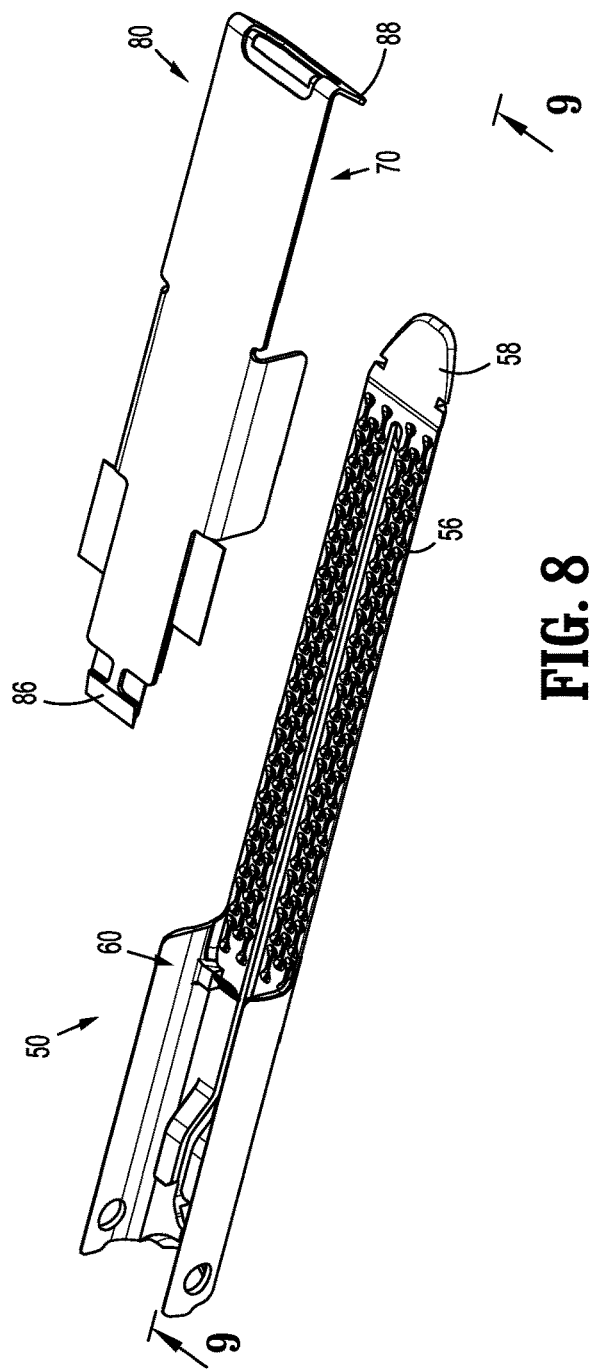
FIG. 8 is a perspective view of the anvil assembly of FIG. 2 and the loaded anvil buttress loading tool of FIG. 7.
Figure 9:
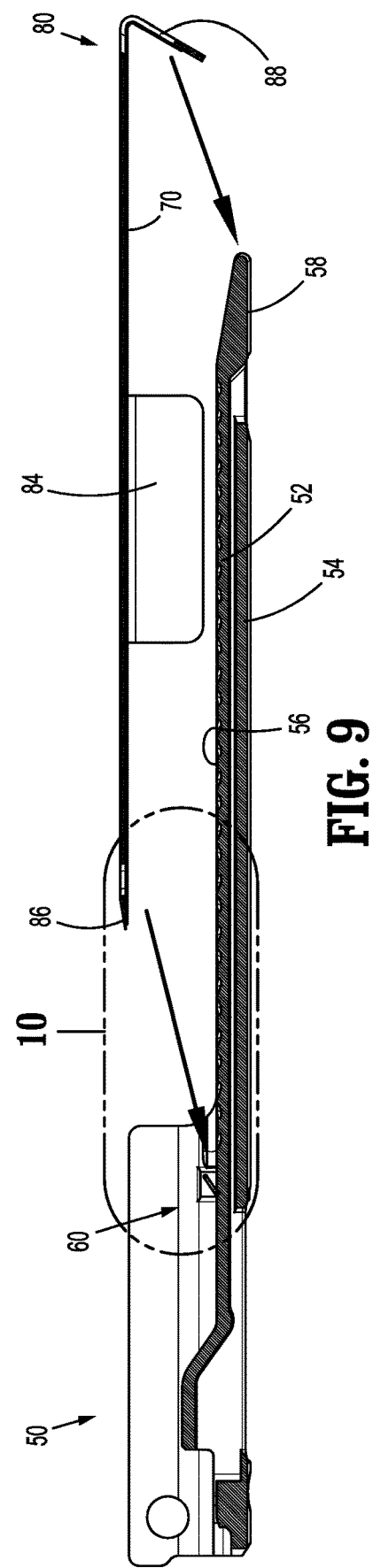
FIG. 9 is a cross-sectional view of the anvil assembly and the loaded anvil buttress loading tool of FIG. 8, taken along section line 9-9 of FIG. 8.
Figure 10:
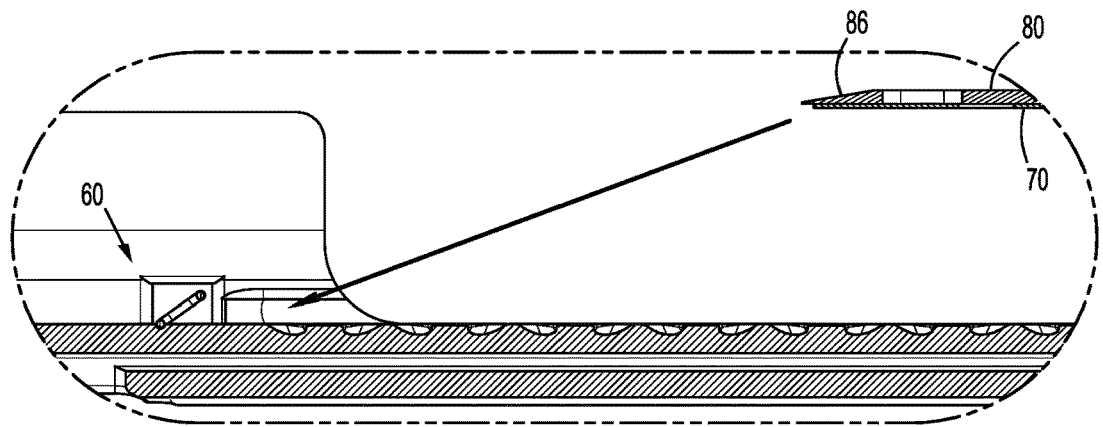
FIG. 10 is a close-up view of the area of detail indicated in FIG. 9.

As shown in FIGS. 8-14, in a method of loading the anvil assembly 50 with the anvil buttress 70, the anvil buttress loading tool 80, loaded with the anvil buttress 70, is positioned relative to the anvil assembly 50 with the anvil buttress 70 facing the tissue facing surface 56 of the anvil assembly 50, as seen in FIG. 8. The loading ramp 86 of the anvil buttress loading tool 80 is distal to and aligned with the pin assembly 60 of the anvil assembly 50, as seen in FIGS. 9 and 10, and the flange 88 of the anvil buttress loading tool 80 is distal to and aligned with the anvil tip 58 of the anvil assembly 50, as seen in FIG. 9.

Figure 11:
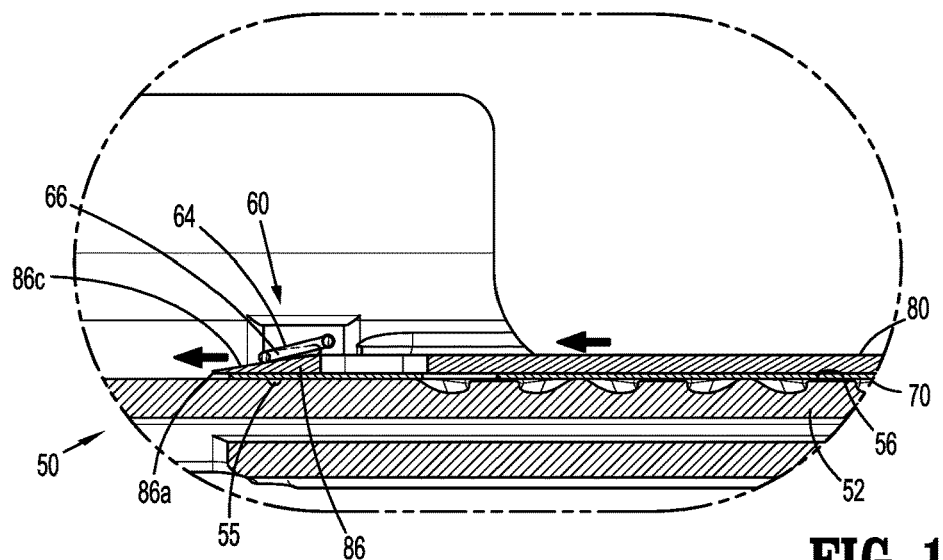
FIG. 11 is a close-up view of the area of detail of FIG. 10, shown with the loaded anvil buttress loading tool partially advanced onto the anvil assembly and the loading ramp of the anvil buttress loading tool engaged with the retaining pins of the pin assembly of the anvil assembly.

The anvil buttress loading tool 80 is placed adjacent to the anvil assembly 50 with the anvil buttress 70 in contact with the tissue facing surface 56 of the anvil assembly 50, as seen in FIG. 11. The anvil buttress loading tool 80 is slid proximally over the anvil assembly 50 and is guided by the longitudinal rails 84 (FIG. 9) to maintain alignment of the anvil buttress loading tool 80 on the anvil assembly 50. During this sliding movement, the proximal end 86a of the loading ramp 86 contacts the retaining pins 64 of the pin assembly 60, pivoting and lifting the bodies 66 of the retaining pins 64 proximally and upwardly out of the groove 55 and away from the tissue facing surface 56 of the anvil plate 52 and along the sloped surface 86c of the loading ramp 86.

Figure 12:
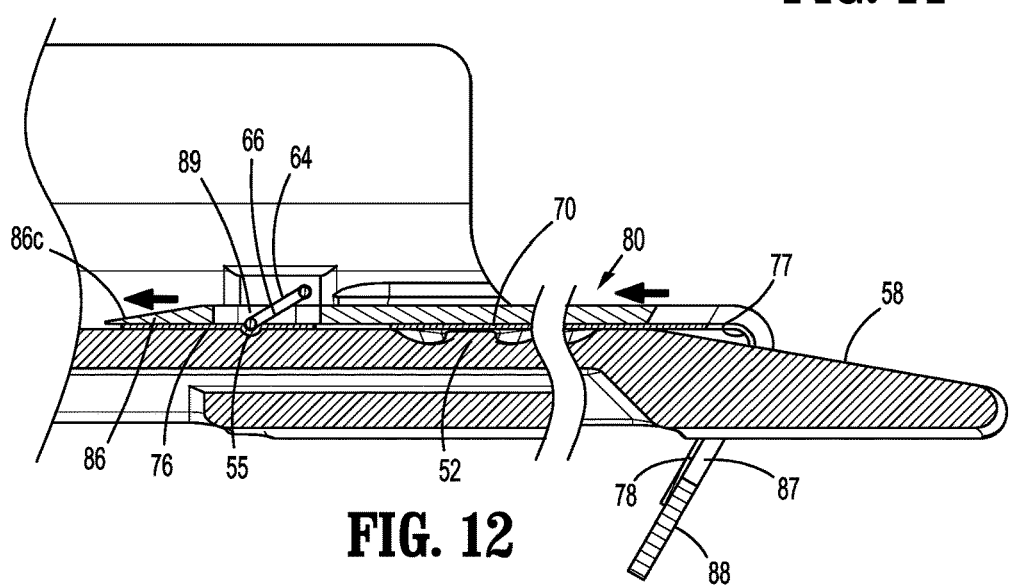
FIG. 12 is a close-up view of proximal and distal portions of the anvil assembly and the loaded anvil buttress loading tool of FIG. 9, shown with the loaded anvil buttress loading tool fully advanced onto the anvil assembly.

The bodies 66 of the retaining pins 64 follow the sloped surface 86c of the loading ramp 86 until the loading ramp 86 clears the retaining pins 64 (e.g., the loading ramp 86 is proximal of the bodies 66) and the bodies 66 snap back down into the groove 55 defined in the anvil plate 52, as seen in FIG. 12, as the retaining pins 64 return to their biased position. The bodies 66 of the retaining pins 64 move into the apertures 89 of the anvil buttress loading tool 80 and capture the proximal tab 76 of the anvil buttress 70 within the groove 55 of the anvil plate 52. In this fully advanced position, the flange 88 of the anvil buttress loading tool 80 is engaged with the anvil tip 58 of the anvil assembly 50 such that the anvil tip 58 extends through the distal opening 87 of the flange 88 and is engaged with the distal tab 78 of the anvil buttress 70 through the distal window 77. It should be understood that additionally or alternatively, the anvil assembly 50 may be slid distally relative to the anvil buttress loading tool 80.

Figures 13, 14:
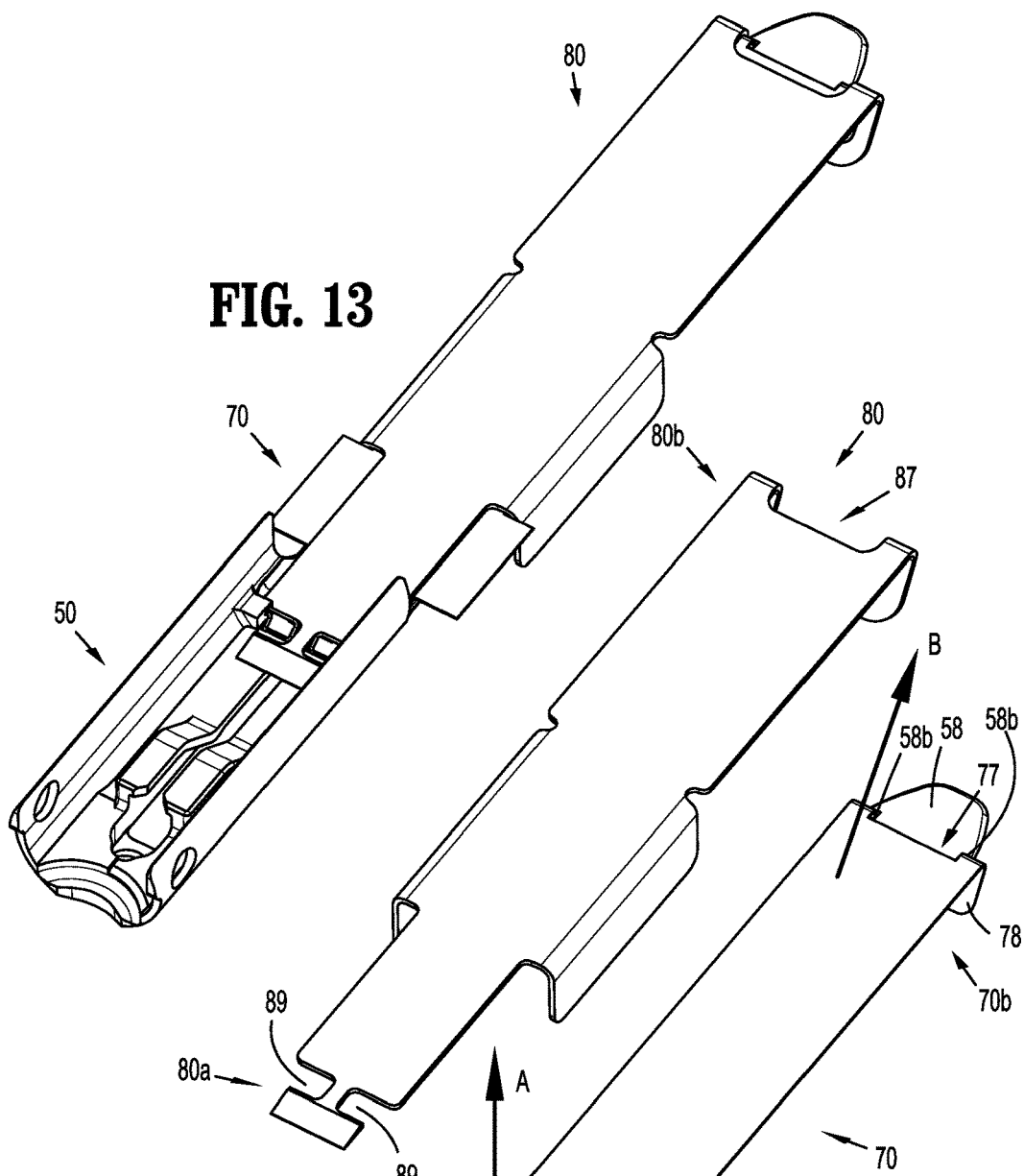
FIG. 13 is a bottom, perspective view of the anvil assembly and the loaded anvil buttress loading tool of FIG. 12.
FIG. 14 is a bottom, perspective view of the anvil assembly and the anvil buttress loading tool of FIG. 13, shown with the anvil assembly loaded with the anvil buttress and the anvil buttress loading tool separated therefrom.

Once the anvil buttress loading tool 80 is fully advanced onto the anvil assembly 50, as seen in FIG. 13, the anvil buttress loading tool 80 is separated from the anvil assembly 50 by lifting the proximal end 80a of the anvil buttress loading tool 80 off of the anvil assembly 50 in the direction of arrow "A," as seen in FIG. 14, so that the anvil buttress loading tool 80 clears the retaining pins 64 of the anvil assembly 50 through the apertures 89. As the proximal end 80a of the anvil buttress loading tool 80 is separated from the anvil assembly 50, the anvil buttress loading tool 80 is moved distally relative to the anvil assembly 50 in the direction of arrow "B," as also seen in FIG. 14, so that the distal end 80b of the anvil buttress loading tool 80 clears the anvil tip 58 of the anvil assembly 50 through the distal opening 87. Additionally or alternatively, the anvil assembly 50 may be moved away from the anvil buttress loading tool 80 in directions opposite arrows "A" and "B."

Figure 15:
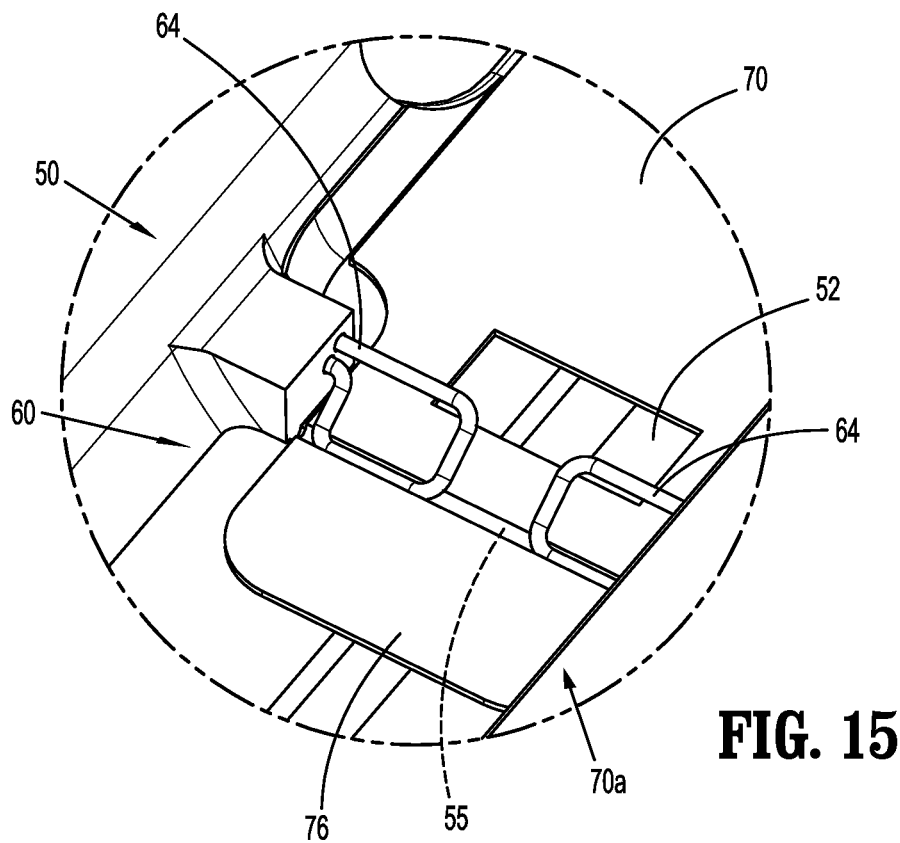
FIG. 15 is a close-up view of the area of detail indicated in FIG. 14, illustrating a proximal portion of the anvil buttress secured to the anvil assembly by the retaining pins of the pin assembly.

After the anvil buttress loading tool 80 is separated from the anvil assembly 50, as seen in FIGS. 14 and 15, a proximal portion 70a of the anvil buttress 70 is retained on the anvil assembly 50 through engagement of the pin assembly 60 capturing the proximal tab 76 between the retaining pins 64 and the groove 55 of the anvil plate 52, and a distal portion 70b of the anvil buttress 70 is retained on the anvil assembly 50 by engagement of the distal tab 78 with the notches 58b of the anvil tip 58 through the distal window 77.

Figure 16:
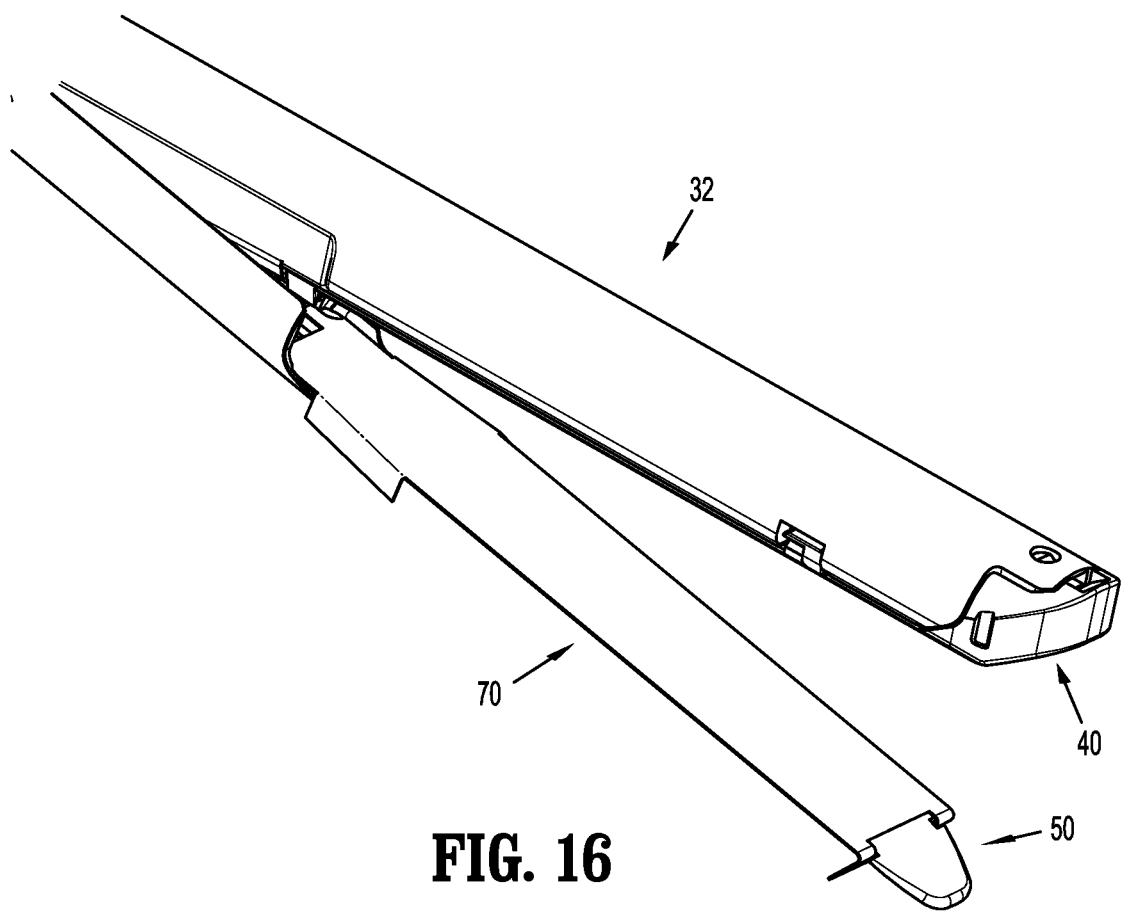
FIG. 16 is a close-up view of the area of detail indicated in FIG. 1, illustrating the anvil assembly of the tool assembly loaded with the anvil buttress.

As shown in FIG. 16, in conjunction with FIG. 1, the surgical stapling apparatus 1, with the anvil assembly 50 loaded with the anvil buttress 70, is ready for use. In aspects, the staple cartridge assembly 40 is pre-loaded and/or loaded with a cartridge buttress (not explicitly shown). The cartridge buttress may be releasably secured to the staple cartridge assembly 40 via any suitable attachment feature within the purview of those skilled in the art, such as, for example, mechanical attachment features (e.g., sutures, pins), chemical attachment features (e.g., adhesive), and/or attachment methods (e.g., welding).

In operation, with the tool assembly 32 loaded with the anvil buttress 70, as described above, the surgical stapling apparatus 1 is used in accordance with methods known by those skilled in the art. Once the staple cartridge and anvil assemblies 40, 50 are clamped onto tissue, the surgical stapling apparatus 1 is fired, thereby stapling the anvil buttress 70 to the tissue, as well as cutting and dividing the tissue and the anvil buttress 70 disposed between the rows of formed staples. When firing is complete and the staple cartridge and anvil assemblies 40, 50 are unclamped, the anvil buttress 70, which is now stapled to the tissue, pulls away from the anvil assembly 50, and the tool assembly 32 can be removed from the surgical site. In some aspects, the used staple cartridge 42 may be removed from the tool assembly 34 and replaced with a new staple cartridge 42 and, in some other aspects, the loading unit 30 may be replaced with a new loading unit 30. A new anvil buttress 70 may be installed onto the anvil assembly 50 by an anvil buttress loading tool 80, as needed or desired, as described above.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A tool assembly comprising:
   a staple cartridge assembly;
   an anvil assembly including an anvil plate and an anvil tip, the anvil plate having a tissue facing surface, a proximal end portion of the tissue facing surface including a pin assembly, wherein the pin assembly of the anvil assembly includes:
   a pair of retaining pins disposed on opposed sides of a central longitudinal slot defined through the tissue facing surface of the anvil plate, each retaining pin including a body positioned against the tissue facing surface and movable relative thereto; and
   a pair of retaining blocks secured to the anvil plate, wherein the pair of retaining pins are coupled to respective ones of the pair of retaining blocks; and
   an anvil buttress including a body disposed over the tissue facing surface, a proximal tab releasably coupled to the anvil assembly by the pin assembly, and a distal tab releasably coupled to the anvil tip, wherein the respective bodies of the pair of retaining pins hold the proximal tab of the anvil buttress against the tissue facing surface.

2. The tool assembly according to claim 1, wherein the tissue facing surface includes a groove defined therein, and the bodies of the pair of retaining pins are biased to extend into the groove.

3. The tool assembly according to claim 1, wherein each retaining pin includes an arm extending laterally from the body and secured to the anvil assembly.

4. The tool assembly according to claim 1, wherein each of the bodies of the pair of retaining pins is disposed at an angle relative to the tissue facing surface of the anvil assembly.

5. The tool assembly according to claim 1, wherein the anvil buttress includes a distal window defined through the distal tab, the distal tab coupled to the anvil assembly by engagement of the distal tab around the anvil tip through the distal window.

6. The tool assembly according to claim 1, wherein the pair of retaining pins are laterally aligned with each other.

7. The tool assembly according to claim 1, wherein the anvil assembly includes an anvil cover disposed over the anvil plate, and the pair of retaining blocks are disposed on an inner surface of the anvil cover.

8. The tool assembly according to claim 1, wherein each retaining pin includes an arm extending from the body, and the arms are non-rotatably secured to the pair of retaining blocks.

9. A tool assembly comprising:
a staple cartridge assembly;
an anvil assembly including:
an anvil plate having:
a tissue facing surface; and
a proximal end portion of the tissue facing surface including a pin assembly; and
an anvil tip, wherein a pair of notches are defined in opposed side edges of the anvil tip; and
an anvil buttress including a body disposed over the tissue facing surface, a proximal tab releasably coupled to the anvil assembly by the pin assembly, and a distal tab releasably coupled to the anvil tip, wherein the distal tab of the anvil buttress is configured to engage the pair of notches.

10. A tool assembly comprising:
an anvil assembly including a tissue facing surface having a central longitudinal slot defined therethrough, the anvil assembly including retaining pins disposed on opposed sides of the central longitudinal slot, each of the retaining pins including an arm secured to the anvil assembly and a body movable in and out of contact with the tissue facing surface, wherein each of the retaining pins is formed from a rod of material that is pre-formed into an open frame defining the body and the arm.

11. The tool assembly according to claim 10, wherein the tissue facing surface includes a groove defined therein, and the bodies of the retaining pins are biased to extend into the groove.

12. The tool assembly according to claim 10, wherein each of the bodies of the retaining pins is disposed at an angle relative to the tissue facing surface of the anvil assembly.

13. The tool assembly according to claim 10, wherein the anvil assembly further includes retaining blocks secured to the anvil assembly, and each of the retaining pins is secured to one of the retaining blocks.

14. The tool assembly according to claim 10, further including an anvil buttress including a body positionable on the tissue facing surface of the anvil assembly, a proximal portion of the anvil buttress releasably securable to the tissue facing surface of the anvil assembly via the retaining pins.

15. The tool assembly according to claim 14, wherein a distal portion of the anvil buttress defines a distal window therethrough, and the distal window is sized and shaped to receive an anvil tip of the anvil assembly to releasably secure the distal portion of the anvil buttress on the anvil assembly.

16. A method of loading an anvil buttress onto an anvil assembly, the method comprising:
applying a force against retaining pins of an anvil assembly that are disposed in a biased position against a tissue facing surface of the anvil assembly to lift the retaining pins off of the tissue facing surface;
passing a proximal portion of an anvil buttress between the retaining pins and the tissue facing surface of the anvil assembly; and
removing the force so that the retaining pins return to the biased position to capture the proximal portion of the anvil buttress between the retaining pins and the tissue facing surface of the anvil assembly.

17. The method according to claim 16, further including sliding an anvil tip of the anvil assembly through a distal window defined in the anvil buttress.

* * * * *